United States Patent [19]

Teicher et al.

[11] Patent Number: 5,679,638
[45] Date of Patent: Oct. 21, 1997

[54] METHOD FOR TREATING A TUMOR WITH A CHEMOTHERAPEUTIC AGENT

[75] Inventors: Beverly A. Teicher, Needham; Carl W. Rausch, Medford; Robert E. Hopkins, 2nd, Scituate, all of Mass.

[73] Assignees: Biopure Corporation, Cambridge; Dana Farber Cancer Institute, Boston, both of Mass.

[21] Appl. No.: 94,501

[22] Filed: Jul. 20, 1993

Related U.S. Application Data

[63] Continuation-in-part of Ser. No. 699,769, May 14, 1991, abandoned.

[51] Int. Cl.[6] .................. A61K 38/42; A61K 38/17; C07K 14/47; C07K 14/805
[52] U.S. Cl. .................. 514/6; 514/21; 514/152; 514/512; 514/568; 514/908; 530/385; 530/829
[58] Field of Search .................. 514/621, 908, 514/512, 568, 152; 530/385; 436/829, 64

[56] References Cited

U.S. PATENT DOCUMENTS

| | | | |
|---|---|---|---|
| 4,001,200 | 1/1977 | Bonsen et al. | 530/385 |
| 4,001,401 | 1/1977 | Bonsen et al. | 514/6 |
| 4,053,590 | 10/1977 | Bonsen et al. | 514/6 |
| 4,738,952 | 4/1988 | Ecanow et al. | 514/6 |
| 4,980,160 | 12/1990 | Goldberg et al. | 424/85.1 |
| 5,084,558 | 1/1992 | Rausch et al. | 530/385 |

FOREIGN PATENT DOCUMENTS

| | | |
|---|---|---|
| 0334576 | 9/1989 | European Pat. Off. |
| PCT/US87/02967 | 10/1987 | WIPO |

OTHER PUBLICATIONS

Teicher, B.A. et al., *Science*, 223:934–936 (1984).
Chang, T.M.S., *Biomat., Art. Cells, Art. Org.*, 16(1–3):11–29 (1988).
De Venuto, F., *Biomat., Art. Cells, Art. Org.*, 16(1–3)77–83 (1988).
Bucci, E. et al., *Biomat., Art. Cells, Art. Org.*, 16(1–3)197–204 (1988).
Teicher, B.A., et al., *Biomat. Art. Cells, Art. Org.*, 16(1–3) 533–546 (1988).
Teicher, B.A., et al., *Int. J. Rad. Oncol. Biol. Physic*, 19:137 (1990) (Abstract).
Teicher, B.A., et al., *Proc. Am. Assoc. Cancer Res.*, 32:387 (1991) (Abstract).
Teicher, B.A., et al., *Biomat., Art. Cells, Art. Org.*,19:491 (1991) (Abstract).
Teicher, B.A., et al., *In. J. Radiation Oncology Biol. Phys.*, 21:969–947 (1991).
Teicher, B.A. et al., *Int. J. Radiat. Oncol. Biol. Phys.*, 19:945–951 (1984).
Teicher, B.A. et al., *Cancer Research*, 47:513–518 (Jan. 15, 1987).
Teicher, B.A. et al., *Proc. Annu. Meet. Am. Assoc. Cancer Res.*, 32:A2302 (1991).
*Chemical Abstracts*, CA101(23):204312S, (Jul. 27, 1984).

*Primary Examiner*—Nancy Degen
*Attorney, Agent, or Firm*—Hamilton, Brook, Smith & Reynolds, PC

[57] ABSTRACT

A method is disclosed treating a tumor in a host by administering a nonemulsified ultrapurified polymerized hemoglobin solution to the host and also administering a chemotherapeutic agent to the host. In a particularly preferred embodiment, the hemoglobin is bovine hemoglobin.

20 Claims, 2 Drawing Sheets

METHOD FOR TREATING A TUMOR WITH A CHEMOTHERAPEUTIC AGENT

RELATED APPLICATIONS

This is a Continuation-In-Part of U.S. Ser. No. 07/699,769 filed May 14, 1991, now abandoned which is hereby incorporated by reference.

GOVERNMENT SUPPORT

Work relating to the invention described and claimed herein was partially supported by Grant No. P01-19589 from the National Institutes of Health and by Grant No. P01-CA38493 from the National Cancer Institute.

BACKGROUND OF THE INVENTION

Solid tumor masses in cancer patients have been found to be heterogeneous in oxygenation and to contain regions of hypoxia. See Vaupel, P., "Oxygenation of Human Tumors", Strahlenther. Onkol. 166:377–386 (1990); and Adams, G. E., The Clinical Relevance of Tumour Hypoxia, 26(4):420–421 (1990). Recent studies in human tumors with oxygen electrodes have reaffirmed the occurrence of significant hypoxic areas within human tumors. Vaupel, P. ibid; Kallinowski, F. et al., "Tumor Tissue Oxygenation as Evaluated by Computerized-pO$_2$-Histography", Int. J. Radiat. Oncol. Biol. Phys. 19:953–961 (1990); and Gatenby, R. A. et al., "Oxygen Distribution in Squamous Cell Carcinoma Metastases and Its Relationship to Outcome of Radiation Therapy", Int. J. Radiat. Oncol. Biol. Phys. 14:831–838 (1988). Preclinical studies, both in vitro and in vivo, have established that hypoxia protects tumor cells from the cytotoxic actions of radiation and chemotherapeutic agents and thereby may be a significant factor in therapeutic resistance. Adams, G. E. ibid; Sartorelli, A. C., "Therapeutic Attack of Hypoxic Cells of Solid Tumors: Presidential Address" Cancer Res. 48:775–778 (1988); Teicher, B. A. et al., "Classification of Antineoplastic Agents by Their Selective Toxicities Toward Oxygenated and Hypoxic Tumor Cells", Cancer Res. 41:73–81 (1981); and Teicher, B. A. et al., "Classification of Antineoplastic Treatments by Their Differential Toxicity Toward Putative Oxygenated and Hypoxic Tumor Subpopulations in vivo in the FSaIIC Murine Fibrosarcoma", Cancer Res. 50:3339–3344 (1990).

Increased delivery of oxygen from the lungs can be a useful way of improving the oxygenation of solid tumor masses by altering the gradient of oxygen as it is absorbed from the vasculature and distributed into the tissue. Because of this, one strategy which has been attempted to overcome the problem of hypoxia in treating tumors involves the use of perfluorocarbon emulsions with oxygen or carbogen (95% oxygen/5% carbon dioxide) breathing. Holden, S. A. et al., "Addition of a Hypoxic Cell Selective Cytotoxic Agent (mitomycin C or porfiromycin) to Treatment with Fluosol®-DA/Carbogen/Radiation", Radiother. Oncol. 18:59–70 (1990); Teicher, B. A. et al., "The Effect of Fluosol-DA and Oxygenation Status on the Activity of Cyclophosphamide In Vivo" Cancer Chemother. Pharmacol. 21:286–291 (1988); Martin, D. F. et al., "Enhancement of Tumor Radiation Response by the Combination of a Perfluorochemical Emulsion and Hyperbaric Oxygen", Int. J. Radiat. Oncol. Biol. Phys. 13:747–751 (1987); Teicher, B. A. and C. M. Rose, "Perfluorochemical Emulsion Can Increase Tumor Radiosensitivity" Science 223:934–936 (1984); and Teicher, B. A. et al., "Optimization of Perfluorochemical Levels with Radiation Therapy" Cancer Res. 49:2693–2697 (1989). In preclinical solid tumor models, the use of perfluorocarbon emulsions with carbogen or oxygen breathing in conjunction with radiation therapy has produced positive results. Teicher, B. A. and C. M. Rose, ibid, Teicher, B. A. et al., ibid; Teicher, B. A. and C. M. Rose, "Oxygen-Carrying Perfluorochemical Emulsion as an Adjuvant to Radiation Therapy in Mice", Cancer Res. 44:4285–4288 (1984); Teicher, B. A. and C. M. Rose, "Effect of Dose and Scheduling on Growth Delay of the Lewis Lung Carcinoma Produced by the Perfluorochemical Emulsion, Fluosol-DA", Int. J. Radiat. Oncol. Biol. Phys. 12:1311–1313 (1986); Teicher, B. A. et al., "Influence of Scheduling Dose and Volume of Administration of the Perfluorochemical Emulsion Therox® on Tumor Response to Radiation Therapy", Int. J. Radiat. Oncol. Biol. Phys., 19:945–951 (1990); Teicher, B. A. et al., "Effect of Fluosol®-DA on the Response of Intracranial 9L Tumors to X-rays and BCNU", Int. J. Radiat. Oncol. Biol. Phys. 15:1187–1192 (1988); Lee, L et al., "Effects of Fluosol-DA and Carbogen on the Radioresponse of SCK Tumors and Skin of A/J Mice", Radiat. Res. 112:173–182 (1987); Martin, D. F. et al., "Effect of a Perfluorochemical Emulsion on the Radiation Response of BA 1112 Rhabdomysarcomas", Radiat. Res. 112:45–53 (1987); Moulder, J. E. et al., "Applicability of Animal Tumor Data to Cancer Therapy in Humans", Int. J. Radiat. Oncol. Biol. Phys. 14:913–927 (1988); Moulder, J. E. and B. L. Fish, "Tumor Sensitization by the Intermittent use of Perfluorochemical Emulsions and Carbogen Breathing in Fractionated Radiotherapy", In: E. M. Fielden, J. F. Fowler, J. H. Hendry and D. Scott (eds.), Proceedings of the 8th International Congress of Radiation Research, Vol. 1, p. 299, London: Taylor and Francis, Inc. (1987); Rockwell, S. et al., "Reactions of Tumors and Normal Tissues in Mice to Irradiation in the Presence and Absence of a Perfluorochemical Emulsion" Int. Radiat. Oncol. Biol. Phys. 112:1315–1318 (1986); Song, C. W. et al., "Increase in pO$_2$ and Radiosensitivity of Tumors by Fluosol®-DA (20%) and Carbogen", Cancer Res. 47:442–446 (1987); and Zhang, W. L. et al., "Enhancement of Tumor Response to Radiation by Fluosol-DA", Int. J. Radiat. Oncol. Biol. Phys. 10:172–175 (1984).

Further, some initial clinical trials of the perfluorochemical emulsion, Fluosol®-DA, and oxygen breathing with radiation therapy have been carried out and some are still underway. Rose, C. M. et al., "A Clinical Trial of Fluosol®-DA 20% in Advanced Squamous Cell Carcinoma of the Head and Neck", Int. J. Radiat. Oncol. Biol. Phys. 12:1325–1327 (1986); Lustig, R. et al., "Phase I-II Study of Fluosol-DA and 100% Oxygen Breathing as an Adjuvant to Radiation in the Treatment of Advanced Squamous Cell Tumors of the Head and Neck", Int. J. Radiat. Oncol. Biol. Phys. 16:1587–1594 (1989); Lustig, R. et al., "Phase I/II Study of Fluosol and 100% Oxygen Breathing as an Adjuvant to Radiation in the Treatment of Unrespectable Non Small Cell Carcinoma of the Lung", Int. J. Radiat. Oncol. Biol. Phys., 17s1:202 (1989); and Evans,R. G. et al., "A Phase I-II Study of the Use of Fluosol®-DA 20% as an Adjuvant of Radiation Therapy in the Treatment of Primary High-Grade Brain Tumors", Int. J. Radiat. Oncol. Biol. Phys., 1721:175 (1989).

The effect of perfluorocarbon emulsions in carbogen or oxygen breathing with certain chemotherapeutic agents has also been studied in preclinical solid tumor models. Teicher, B. A. et al., "Classification of Antineoplastic Treatments by Their Differential Toxicity Toward Putative Oxygenated and Hypoxic Tumor Subpopulations in vivo in the FSaIIC Murine Fibrosarcoma", Cancer Res. 50:3339–3344 (1990);

Holden, S. A. et al., "Addition of a Hypoxic Cell Selective Cytotoxic Agent (Mitomycin C or Porfiromycin) to Treatment with Fluosol-DA®/Carbogen/Radiation", Radiother. Oncol. 18:59–70 (1990); Teicher, B. A. et al., "The Effect of Fluosol-DA and Oxygenation Status on the Activity of Cyclophosphamide in vivo" Cancer Chemother. Pharmacol. 21:286–291 (1988); Teicher, B. A. et al., "Approaches to Defining the Mechanism of Fluosol-DA 20%/Carbogen Enhancement of Melphalan Antitumor Activity", Cancer Res. 47:513–518 (1987); Teicher, B. A. et al., "Differential Enhancement of Melphalan Cytotoxicity in Tumor and Normal t+Tissue by Fluosol-DA and Oxygen Breathing", Int. J. Cancer 36:585–589 (1985); Teicher, B. A. et al., "Effects of Various Oxygenation Conditions on the Enhancement by Fluosol-DA of Melphalan Antitumor Activity", Cancer Res. 47:5036–5041 (1987); Teicher, B. A and S. A. Holden, "A Survey of the Effect of Adding Fluosol-DA 20%/$O_2$ to Treatment with Various Chemotherapeutic Agents", Cancer Treat. Rep. 71:173–177 (1987); Teicher, B. A. et al., "Effect of Various Oxygenation Conditions and Fluosol-DA on Cancer Chemotherapeutic Agents" Biomat., Art. Cells and Art. Organs 16:533–546 (1988); Teicher, B. A. et al., "Effect of Oxygen on the Cytotoxicity of Antitumor Activity of Etoposide", J. Natl. Cancer Inst. 75:1129–1133 (1985); Teicher, B. A. et al., "Effect of Fluosol-DA/$O_2$ on Tumor Cell and Bone Marrow Cytotoxicity of Nitrosoureas in Mice Bearing FSaII Fibrosarcoma", Int. J. Cancer 38:285–288 (1986); Teicher, B. A. et al., "Effect of Fluosol-DA/$O_2$ on the Antitumor Activity and Pulmonary Toxicity of Bleomycin", Cancer Chemother. Pharmacol. 18:213–218 (1986); Teicher, B. A. et al., "Effects of Fluosol®-DA and Oxygen Breathing on Adriamycin Antitumor Activity and Cardiac Toxicity in Mice", Cancer 61:2196–2201 (1988); Teicher, B. A. et al., "Effect of Carious Oxygenation Conditions and Fluosol®-DA on the Cytotoxicity and Antitumor Activity of Bleomycin", J. Natl. Cancer Inst. 80:599–603 (1988); Teicher, B. A. et al., "Effect of Fluosol-DA/Carbogen on Etoposide/Alkylating Agent Anti-tumor Activity", Cancer Chemother Pharmacol 21:281–285 (1988); Martin, D. F. et al., "Potentiation of Rat Brain Tumor Therapy by Fluosol and Carbogen", NCI Monogr. 6:119–122 (1988); and Kim. G. E. and C. W. Song, "The Influence of Fluosol-DA and Carbogen Breathing on the Antitumor Effects of Cyclophosphamide In Vivo", Cancer Chemother. Pharmacol. 25:99–102 (1989). With many chemotherapeutic agents, very positive therapeutic results have been obtained and several initial clinical trials have been carried out with Fluosol®-DA and oxygen breathing with single anticancer drugs. See Gruber, M. et al., "Phase I/II Study of Fluosol®/$O_2$ in Combination with BCNU in Malignant Glioma", Proc. Amer. Assoc. Cancer Res. 31:190 (March 1990); Carewal, H. et al., "Fluosol®/Oxygen in Combination with Cyclophosphamide in Advanced Non-Small Cell Lung Carcinoma (NSCLC): Phase I Results", Proc. Amer. Assoc. Cancer Res. 30:271 (March 1989); and Meyers, F. et al., "Phase I/II Study of Fluosole®/Oxygen in Combination with Weekly 5-Fluorouracil (5FU) in Metastatic Colorectal Carcinoma", Proc. Amer. Assoc. Cancer. Res. 30:256 (March 1989).

Despite the initial success with the use of perfluorocarbon emulsions, combined with carbogen or oxygen breathing in conjunction with chemotherapeutic agents, these techniques have not proven entirely satisfactory. For example, perfluorocarbons have very limited oxygen-transport capability at ambient oxygen pressures. Blood delivers approximately 6% (v/v) oxygen to tissues at ambient pressures, whereas, at these same pressures, perfluorocarbon emulsions can only deliver about 2% (v/v). Furthermore, generally perfluorocarbons only enhance the anti-tumor effects of the chemotherapeutic agents while retained in the body and only while breathing an enriched supply of oxygen, such as pure oxygen or carbogen. When not breathing enriched oxygen, perfluorocarbons typically do not enhance the effect of chemotherapeutic agents. In addition, the retention time of most perfluorocarbons in the body is unacceptably low.

Thus, the need exists for a method of enhancing the effects of antitumor chemotherapeutic agents for longer periods of time while breathing air or oxygen-enriched atmospheres.

SUMMARY OF THE INVENTION

This invention relates to a method for treating a tumor in a host, including a human being, with a chemotherapeutic agent. In this method, a nonemulsified ultrapurified polymerized hemoglobin solution is administered to the host in an amount which significantly increases the antitumor effect of the chemotherapeutic agent. An effective amount of the chemotherapeutic agent is also administered to the host. In a particularly preferred embodiment, the hemoglobin is bovine hemoglobin.

The advantages of administering a nonemulsified ultrapurified polymerized hemoglobin solution with a chemotherapeutic agent include a significant improvement in tumor oxygenation and an increase in the antitumor effect of the chemotherapeutic agent even without carbogen or pure oxygen breathing therapy. This enhanced effect can occur while just breathing air. Thus, while sufficient amounts of the chemotherapeutic agent and of the polymerized hemoglobin solution are in the body, the antitumor effect will be enhanced. In addition, as hemoglobin is able to chelate and deliver oxygen under air-breathing conditions, oxygen toxemia, which can occur with the use of perfluorocarbon emulsions, is eliminated by the use of the hemoglobin solution. Further, polymerized hemoglobins typically have a longer circulating half-life than many of the perfluorocarbon emulsions and, therefore, have a longer functional period post-administration. The acidic environments in tumors increases the off-loading of oxygen and, therefore, the oxygen delivery from hemoglobin, as should temperature elevation (i.e., clinical hyperthermia). Hemoglobin solutions also have less retention in normal tissues, which is a concern with many perfluorocarbon preparations.

DETAILED DESCRIPTION OF THE INVENTION

Figure 1:
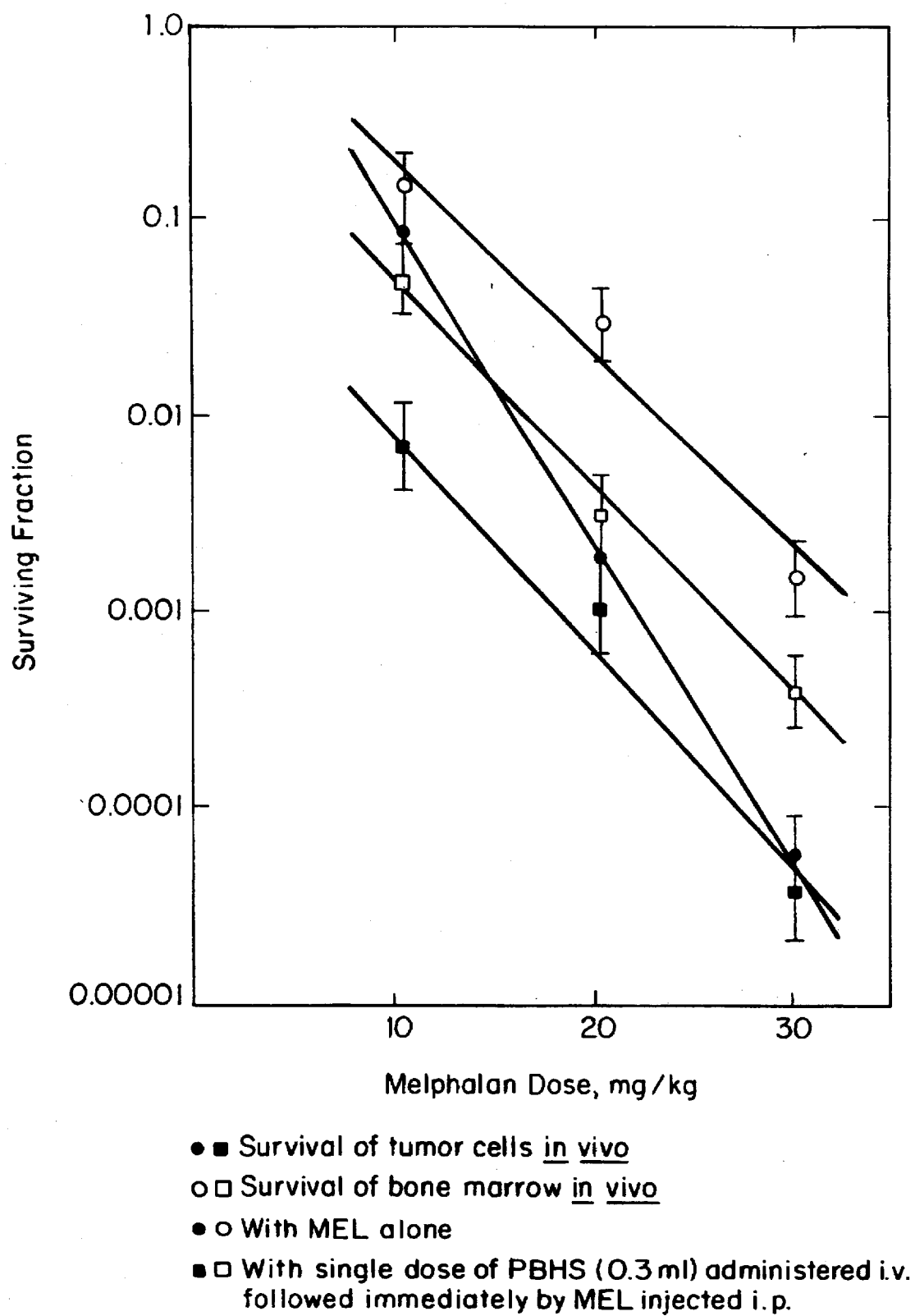
FIG. 1 is a plot of the surviving fraction of FSaIIC tumor cells and bone marrow granulocyte-macrophage colony forming units (CFU-GM) versus dose of Melphalan (PAM) administered to mice alone or with a single dose of ultrapurified polymerized bovine hemoglobin solution (UPHS) administered immediately prior to PAM injection.

This invention relates to a method for treating a tumor in a host. The host can be any species which develops solid tumors or masses of tumor cells containing oxygen heterogeneity. Examples of hosts include but are not limited to, reptiles, amphibians, avians and mammals, including human beings, as well as domestic animals such as dogs, cats, cows and horses.

Tumors treatable by this method include those in which oxygen heterogeneity, including regions of hypoxia, protect tumor cells against the cytotoxic action of chemotherapeutic agents. These are usually solid tumors, such as sarcomas, carcinomas, lymphomas, etc. However, in certain cases of dispersed tumor cells, such as advanced leukemia, masses of tumor cells form which can produce regions of oxygen heterogeneity, as well.

As used herein, the term "chemotherapeutic agent" is employed to include chemical and biological agents, including small molecules and larger molecules, such as peptides, proteins, lymphokines, antibodies, tumor necrosis factor, conjugates of antibodies with toxins, and other chemical or biological molecules which have an antitumor effect which is oxygen dependent.

There are a variety of known classes of small molecule antitumor chemotherapeutic agents. These include alkylating agents, such as Melphalan (PAM), Cyclophosphamide (CTX), cis-Diammminedichloroplatinum (II) (CDDP) and N,N'-bis(II-chloroethyl)-N-nitrosourea (BCNU). Another general class of antitumor chemotherapeutic agents are the antimetabolites, such as 6-Mercaptopurine, 5-fluorouracil (5-FU), fluorodeoxyuridine, cytosine arabinoside, methotrexate and thioquinone. Antibiotics are another general class of antitumor chemotherapeutic agents including drugs such as actinomycin, daunorubicin, adriamycin and bleomycin. Still yet another class is the vinca alkaloids, including etoposide, vincristine and vinblastine.

Mixtures of more than one antitumor chemotherapeutic agent can, of course, be administered. Indeed, it is often preferred to use mixtures or sequential administration of different antitumor agents to treat tumors, especially agents from the different classes of agents. For example, mixtures of methotrexate and a cis-platinum compound are often used to treat various tumors.

The chemotherapeutic agent can be administered to the host parenterally, for example, by subcutaneous, intravenous or intramuscular injection or by absorption through a bodily tissue, such as the digestive tract, the respiratory system or the skin. The form in which the antitumor agent is administered (e.g., capsule, tablet, solution, emulsion) will depend, at least in part, on the route by which it is administered.

The chemotherapeutic agent is administered in a therapeutically effective amount. This amount will be determined on an individual basis and will be based, at least in part, on consideration of the host's size, the specific tumor to be treated, the severity of the symptoms to be treated, the results sought, and other such considerations. An effective amount can be determined by one of ordinary skill in the art employing such factors and using no more than routine experimentation.

In one embodiment, in order to increase oxygen transport to the site of a tumor, a nonemulsified ultrapurified polymerized hemoglobin solution (UPHS) is administered to the host. Although not essential, it is preferred to administer the UPHS prior to administration of the antitumor agent. Also, the hemoglobin solution is preferably administered intravenously so that it is taken up into the bloodstream of the host immediately.

The amount of time between the administration of the hemoglobin solution and chemotherapeutic agent will depend upon factors such as the amount of time it takes the hemoglobin solution to be fully incorporated into the circulatory system of the host and the retention time of the hemoglobin solution in the host's body. Since UPHS has been found to remain in the host's blood stream for up to at least 48 hours, a variety of times during this period are sufficient.

Hemoglobin sufficient for UPHS can be derived from a wide variety of sources. These sources include human blood, such as outdated blood bank supplies. Additionally, hemoglobin can be derived from a variety of mammalian sources such as horses, pigs, cows, sheep, etc.

In a preferred embodiment, the hemoglobin will be derived from a species in which the hemoglobin is chloride ion-dependent for oxygen transport rather than dependent upon 2,3-diphosphoglycerate (2,3-DPG) or other phosphate molecules. This is because 2,3-DPG, present in human red blood cells, is not available freely in the circulatory system of the host to effect oxygen uptake and release for hemoglobin solutions administered according to this invention. Thus, it is preferred to employ a hemoglobin which is chloride ion-dependent for oxygen transport, such as those hemoglobins derived from sheep, goats, cows and cats. See Bunn, H. F., "Differences in the Interaction of 2,3-Diphosphoglycerate with Certain Mammalian Hemoglobins", *Science* 172:1049–50 (1971); Breepoel, P. M. et al., "Interaction of Organic Phosphates with Bovine Hemoglobin—I Oxylabile and Phosphate Labile Proton Binding", *Pflugers Arch.* 389:219–25 (1981); and Fronticelli, C. et al., "Solvent Regulation of Oxygen Affinity and Hemoglobin—Sensitivity of Bovine Hemo-Globin to Chloride Ions", *J. Biol. Chem.* 259:10841–4 (1984). Bovine hemoglobin is particularly preferred because of its proven ability to transport oxygen in human beings and other mammals, in a chloride-ion dependent way, and because of its low antigenicity in human beings when it has been ultrapurified.

In order to increase the useful life of hemoglobin in the circulation, it is polymerized or cross-linked by a variety of techniques. Cross-linking agents include dialdehydes, such as glyoxal, malonic dialdehyde, succinic dialdehyde, glutaraldehyde, adipaldehyde, 3-methyl-glutaraldehyde, propyladipaldehyde, phthalic dialdehyde, terephthaldehyde and malonic dialdehyde have been employed. See, in this regard, Bonsen et al., U.S. Pat. Nos. 4,001,200; 4,001,401; and 4,053,590; Bonhard et al., U.S. Pat. Nos. 4,136,093 and 4,336,248; the teachings of each of which are incorporated herein by reference.

The polymerized hemoglobin solution is ultrapurified by various filtration and chromatographic procedures which have been described heretofore in the art. An ultrapure hemoglobin solution, according to this invention, is a hemoglobin solution which is substantially free of stroma, endotoxin, other pyrogenic substances, phospholipids, immunoglobulins and cellular-contained enzymes.

A particularly preferred nonemulsified ultrapure polymerized hemoglobin solution is based upon bovine hemoglobin. Such a bovine blood substitute has an endotoxin concentration of less than 0.5 endotoxin units/ml as measured by the LAL test; a phospholipid concentration of less than about 1 nanogram/milliliter and has a molecular weight distribution greater than 90% in the range of 65,000–1,000,000 daltons. This bovine hemoglobin solution also has an osmolarity measured by freezing point depression in the range of 180–320 milliosmols per liter; a hemoglobin content of 5–25 grams per deciliter; a met hemoglobin content of less than 20%; a $p_{50}$ in the range of 18–37 mmHg; an intravascular half life of at least two days; a cross-linking profile on gel permeation chromatography of greater than 70% cross-linked.

Such nonemulsified ultrapurified polymerized bovine hemoglobin solution is made and sold by Biopure Corporation, Boston, Mass. under the trademark Hemopure.

This and other ultrapurified hemoglobin solutions are described in U.S. Pat. No. 5,084,558 issued to Rausch et al., the teachings of which are hereby incorporated by reference.

Appropriate dosages of UPHS can be determined by those skilled in the art using routine experimentation. The dose employed in the murine studies in the Examples herein was 8–12 ml/kg, which is 9%–15% of the estimated circulatory volume. This dose corresponds to 500–750 ml as the comparative human dose or 11%–19% of estimated circulatory volume. Multiple doses of UPHS, for example one before each chemotherapy treatment, are, of course; useful with this invention and can be preferred in many cases.

In another embodiment UPHS is administered contemporaneously with treatment with an enzyme cyclooxygenase inhibitor. Examples of said inhibitors include non-steroidal anti-inflammatory drugs (NSAID), such as minocycline hydrochloride (Mino), Diflunisal (Diflun) or Sulindac (Sulin). The addition of an enzyme cyclooxygenase inhibitor to the treatment enhances the anti-tumor affects of the chemotherapeutic agent by blocking the metabolism of arachidonic acid to inhibit cell regulation processes.

Appropriate dosages of NSAIDS can be determined by those skilled in the art using routine experimentation. The dose employed in the murine studies in the Examples herein was a 10 mg/kg dose given daily.

The techniques for treating tumors described herein can be employed at normal body temperatures or at elevated body temperatures (hyperthermia).

Although not required, it is sometimes preferred to have the host breathe oxygen-enriched gas prior to and/or post administration of the anti-tumor therapeutic agent. This can be done by having the host breathe oxygen-enriched air, 100% oxygen or carbogen (95% oxygen/5% CO2), or in certain cases exposing the host to hyperbaric oxygen conditions.

This invention will now be further and more specifically described by the following examples.

EXAMPLE I

FSaII Fibrosarcoma Growth

The FsaII fibrosarcoma (FSaIIC), adapted for growth in culture, was employed. See Rice, L. et al., "The Radiosensitivity of a Murine Fibrosarcoma as Measured by Three Cell Survival Assays", Br. J. Cancer 41:240–245 (1980). $2 \times 10^6$ FSaIIC cells, prepared from a brei of several stock tumors, were implanted intramuscularly into the legs of 8- to 10-week old male C3H/FeJ mice (The Jackson Laboratory, Bar Harbor, Me.). When the tumors were approximately 100 $mm^3$ in volume, 0.3 ml (12 ml/kg; 1.32 gm protein/kg) of UPHS was injected via the tail vein. The UPHS solution was obtained from Biopure Corporation, Boston, Mass. and was a polymerized form of a highly purified bovine hemoglobin solution. It contained 11±2 gm/deciliter of bovine hemoglobin. Measurements of $p_{50}$ for the UPHS in three assay systems and under conditions designed for testing human hemoglobin gave values of 17 mmHg to 23 mmHg. The hemoglobin content had a molecular weight of range from 68,000 to 1,000,000 (w/v). It contained sodium (145 mM/L), chloride (140 mM/L) and potassium (4.0 mM/L) in a buffer solution (pH 7.8±0.4). The circulating half life of this UPHS was about 2.5 days. DeVenuto, F., "Evaluation of Human and Bovine Modified-Hemoglobin Solution as Oxygen-Carrying Fluid for Blood Volume Replacement", Biomat. Art. Cells, Art. Org. 16:77–82 (1988); and Winslow, R. M., "Optimal Hematologic Variables for Oxygen Transport Including $p_{50}$, Hemoglobin Cooperativity, Hematocrit, Acid-Base Atatus, and Cardiac Function", Biomat., Art. Cells and Art. Organs 16:149–172 (1988).

Immediately after the administration of UPHS, 10 mg/kg Melphalan (PAM), 150 mg/kg Cyclophosphamide (CTX), 10 mg/kg cis-diaminodichloroplatinum(II) (CDDP) or 15 mg/kg N,N-bis(2-chloroethyl)-N-nitrosourea (BCNU) was administered by intraperitoneal injection of 0.2 ml of phosphate buffered normal saline containing the drug. CTX and PAM were purchased as pure powders from Sigma Chemical Company, St. Louis, Miss. CDDP was obtained as a gift from Bristol Meyers-Squibb Company, Wallingford, Conn. BCNU (Carmustine) was purchased from the Dana-Farber Cancer Institute Pharmacy.

The mice were allowed to breathe air or were placed in a circulating atmosphere of 95% $O_2$/5% $CO_2$ (carbogen) for six hours and then removed to air. The progress of each tumor was measured three times weekly until it reached a volume of 500 $mm^3$. Tumor growth delay was calculated as the days taken by each individual tumor to reach 500 $mm^3$ compared to the untreated controls. Each treatment group had seven animals and the experiment was repeated three times. Days of tumor growth Relay are the mean ±SE for the treatment group compared to the control.

Data on the delay of tumor growth were analyzed with a BASIC program for the Apple II minicomputer. The program derives the best fit curve for each set of data, then calculated the median, mean and standard error of the mean for individual tumor volumes and the day on which each tumor reached 500 $mm^3$. Statistical comparisons were made with Dunn Multiple Comparisons Test.

The results of these tumor growth delay experiments are presented below in Table I.

TABLE I

TUMOR GROWTH DELAYS (DAYS)

| Treatment Group | Alkylating Agent(alone) | UPHS/Air | Carbogen | UPHS/Carbogen |
|---|---|---|---|---|
| PAM(10 mg/kg) | 3.1 ± 0.5 | 6.9 ± 1.0 | 4.0 ± 0.6 | 11.1 ± 1.3 |
| CTX(150 mg/kg) | 3.6 ± 0.4 | 7.4 ± 0.7 | 5.0 ± 0.5 | 16.5 ± 1.8 |
| CDDP(10 mg/kg) | 7.4 ± 0.8 | 9.6 ± 1.1 | 7.6 ± 0.3 | 14.1 ± 1.6 |
| BCNU(15 mg/kg) | 2.5 ± 0.3 | 3.8 ± 0.5 | 3.3 ± 0.3 | 5.7 ± 0.9 |

Neither UPHS/Air nor UPHS/carbogen, without a cytotoxic agent, had any effect on the growth of the FSaIIC fibrosarcoma. The addition of UPHS to treatment with PAM resulted in a 2.2-fold increase in the tumor growth delay produced by PAM from about 3 days to about 7 days. Although carbogen breathing (6 hours) resulted in a small increase in tumor growth delay compared with PAM and air breathing, the combination of UPHS and carbogen produced a 3.6-fold increase in the tumor growth delay compared with PAM alone. The addition of UPHS to treatment with a single dose of CTX resulted in a 2.1-fold increase in the tumor growth delay produced by CTX alone. Breathing a carbogen atmosphere for 6 hours post drug administration resulted in a small increase in the tumor growth delay produced by CTX; however, the combination of UPHS and carbogen breathing was much more effective resulting in a 4.6-fold increase in tumor growth delay to about 16.5 days from 3.6 days for the drug alone.

The tumor growth delay produced by CDDP was less affected by the addition of UPHS to treatment with the drug than was either PAM or CTX. There was only a 1.3-fold increase in tumor growth delay with UPHS and CDDP compared with CDDP alone. Carbogen breathing for 6 hours following drug administration had no significant effect on the tumor growth delay produced by CDDP. The combination of UPHS and carbogen breathing was a more effective addition to treatment with CDDP and resulted in a 1.9-fold increase in tumor growth delay from 7.4 to 14.1 days.

The addition of UPHS to treatment with BCNU increased the tumor growth delay produced by BCNU by 1.5-fold. Although carbogen breathing for 6 hours post drug administration increased the tumor growth delay produced by BCNU to a small degree, a much larger enhancement in tumor growth delay was observed with UPHS and carbogen breathing in combination with BCNU. The combination of UPHS/BCNU and carbogen resulted in a tumor growth delay of about 5.7 days, which was a 2.3-fold increase over the 2.5 days obtained with BCNU alone.

EXAMPLE II

Effects of UPHS on FSaII Fibrosarcoma Cell Toxicity and Bone Marrow Toxicity of PAM The procedures and materials of Example I were employed, except as noted. In this Example, tumors were allowed to grow to approximately 100 mm$^3$ in volume, which took about one week after tumor cell implantation. At this time, 0.3 ml of UPHS was injected via the tail vein. Immediately afterward, PAM was administered by intraperitoneal injection. The animals were then allowed to breathe air or were placed in a circulating atmosphere of carbogen for 6 hours and then removed to air. The mice were sacrificed 24 hours after treatment to allow for full expression of drug cytotoxicity and repair of potentially lethal damage. The tumors were excised under sterile conditions and single cell suspensions were prepared for a colony forming assay. See Teicher, B. A. et al., "Approaches to Defining the Mechanism of Fluosol-DA 20%/Carbogen Enhancement of Melphalan Antitumor Activity", *Cancer Res.* 47:513–518 (1987); Teicher, B. A. et al., "Differential Enhancement of Melphalan Cytotoxicity in Tumor and Normal Tissue by Fluosol-DA and Oxygen Breathing", *Int. J. Cancer* 36:585–589 (1985); Teicher, B. A. et al., "Effects of Various Oxygenation Conditions on the Enhancement by Fluosol-DA of Melphalan Antitumor Activity", *Cancer Res.* 47:5036–5041 (1987); Teicher, B. A. and S. A. Holden, "A Survey of the Effect of Adding Fluosol-DA 20%/O$_2$ to Treatment with Various Chemotherapeutic Agents", *Cancer Treat. Rep.* 71:173–177 (1987), Teicher, B. A. et al., "Effect of Various Oxygenation Conditions and Fluosol-DA on Cancer Chemotherapeutic Agents", *Biomat., Art. Cells and Art. Organs* 16:533–546 (1988). One week later, the plates were stained with crystal violet and colonies of more than 50 cells were counted. The untreated tumor cell suspensions had a plating efficiency of 8–12%.

Bone marrow toxicity was determined as follows. Bone marrow was taken from the same animals used for the tumor excision assays and colony forming assays were carried out in the same manner. Colonies of at least 50 cells were scored on an acculite colony counter (Fisher, Springfield, N.J.). The results from three experiments, in which each group was measured in triplicate, were averaged.

The result for the tumor excision assays and bone marrow toxicity tests with PAM are plotted in FIG. 1 wherein the surviving fraction +SE of cells from the treated groups are compared to untreated controls.

PAM killed FSaIIC cells in a log-linear manner with increasing dose of PAM. With addition of UPHS to treatment with PAM at a dose of 10 mg/kg, there was about a 10-fold increase in tumor cell killing compared with PAM alone. At higher doses of PAM, the enhancement in tumor cell killing with the combination treatment disappeared indicating that whatever effect UPHS had to effect tumor cell killing could also be accomplished by increased dosage of the alkylating agent. In the bone marrow CFU-GM, the addition of UPHS to treatment with PAM produced a 3-fold increase in cell killing across the entire dosage range of PAM examined.

EXAMPLE III

Figure 2:
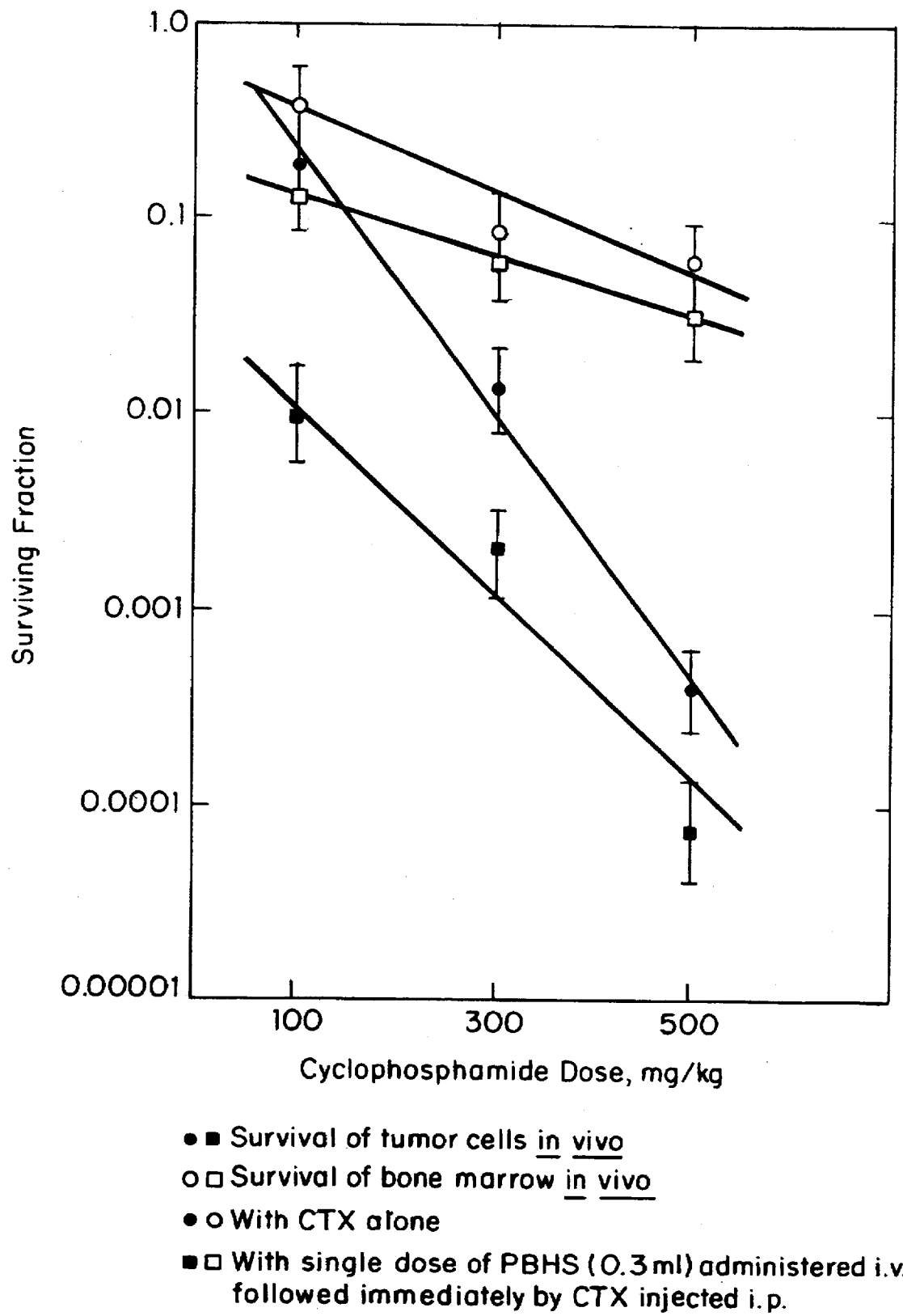
FIG. 2 is a plot of the surviving fraction of FSaIIC tumor cells and bone marrow CFU-GM versus dose of Cyclophosphamide (CTX) administered to mice alone or with a single dose of UPHS immediately prior to CTX injection.

Effects of UPHS on FSaII Fibrosarcoma Cell Toxicity and Bone Marrow Toxicity of CTX The procedures and materials of Example II were employed except that CTX was administered instead of PAM. The results are shown in FIG. 2.

CTX killed increasing numbers of FSaIIC cells with increasing doses of the drug. The addition of UPHS to treatment with a dose of 100 mg/kg of CTX resulted in about a 20-fold increase in the killing of FSaIIC cells. Although the differential between tumor cell kill by CTX alone and CTX plus UPHS decreased as the dose of CTX was increased, at the highest dose (500 mg/kg) of CTX examined, there was about 9-fold greater kill of FSaIIC tumor cells with the combined treatment. The addition of the UPHS to treatment with CTX resulted in a 2–3-fold increase in the toxicity of the drug to bone marrow CFU/gm.

EXAMPLE IV

Intracranial and Subcutaneous 9L Gliosarcoma

The 9L gliosarcoma has been widely used as a model for brain tumors. Barker, M. et al., "Development of an Animal Brain Tumor Model and Its Response to Therapy with 1,3-Bis(2-chloroethyl)-1-nitrosourea", *Cancer Res.* 33:976–986 (1973) and Levin, V. A. et al., "Effectiveness of the Nitrosourea as a Function of Lipid Solubility for the Chemotherapy of Experimental Rat Brain Tumors", *Cancer Chemother. Rep.* 58:787–792 (1974). Furthermore, the 9L gliosarcoma growing subcutaneously in the hind leg of the Fisher 344 rat contains major areas of severe (<5 mmHg) hypoxia making up about 49% of the tumor.

The 9L gliosarcoma (9L) cells were obtained as a gift of 9L/SF gliosarcoma cells from Dr. Dennis Dean, University of California, San Francisco. These cells were maintained in culture in ∝-MEM (Grand Island Biological Co., Grand Island, N.Y.) and supplemented with 10% fetal bovine serum (Sterile Systems, Inc., Logan, Utah) and with antibiotics. The 9L cells (4×10$^4$) in 10 μL of media without serum were implanted intracranially in male Fischer 344 rats (Taconic Farms, Germantown, N.Y.) weighing 200–250 gm on day 0. Each rat was anesthetized with sodium pentobarbital. A midline scalp incision was made and a hole was bored through the skull with 23 gauge needle at a point 2 mm lateral to the midline. The cell suspension was injected into the right frontal lobe at a depth of 3 mm from the dural surface. The needle was removed and the hole filled with dental cement. The scalp was sealed with a surgical clip. Two days later 9L cells (2×10$^6$) were implanted subcutaneously into the flank of each animal. When the tumors were approximately 100 mm$^3$ in volume, 7 days after tumor cell implantation, 8 ml/kg of UPHS was injected via the tail vein. After injecting the UPHS, administration of chemotherapeutic agents was initiated. CDDP therapy consisted of a single 8 mg/kg CDDP dose administered by intraperitoneal injection on day 7. BCNU therapy consisted of three 15 mg/kg BCNU doses administered by intraperitoneal injection days 7, 9 and 11. CTX and ifosfamide (IFOS) therapy consisted of three 100 mg/kg CTX or IFOS doses administered by intraperitoneal injection on days 7, 9 and 11. For the BCNU, CTX and IFOS therapies, UPHS was intravenously administered prior to each chemotherapeutic agent injection on days 7, 9 and 11. The IFOS was purchased from the Dana-Farber Cancer Institute. Survival of animals was monitored daily. Animals that were moribund or unable to reach food or water were killed by $CO_2$ inhalation.

The progress of each subcutaneous tumor was measured 3 times/week until it reached a volume of 500 mm³. Tumor growth delay was calculated as the number of days for each individual tumor to reach 500 mm³ compared with untreated controls. Each treatment group had 4 animals and the experiment was repeated twice. Days of tumor growth delay are the mean ±SE for the treatment group compared with the control.

The increases in life span for rats with intracranial 9L tumors are presented below in Table II.

TABLE II

Life Span Increase

| Treatment Group | Survival Days | % Increased from Control |
|---|---|---|
| Control Group | 26 ± 2.2 | 0% |
| UPHS | 27.8 | 7% |
| BCNU | 31.6 | 22% |
| BCNU/UPHS | 35.9 | 38% |
| CTX | 31.3 | 20% |
| CTX/UPHS | 37.2 | 43% |
| CDDP | 33.6 | 29% |
| CDDP/UPHS | 38.0 | 46% |
| IFOS | 30.9 | 19% |
| IFOS | 35.9 | 38% |

The effect of the treatments on the growth of the intracranial tumor was determined by the increase in life span of treated groups compared with the untreated controls. A percentage increase in life span of 25% or more is therapeutically significant. Although BCNU, CTX or IFOS alone improved the survival of the animals, the increase in life span did not reach significance. CDDP treatment alone resulted in a significant increase in life span. However with administration of UPHS prior to the BCNU, CTX, CDDP or IFOS therapy, substantially larger increases in life span of 38%, 43%, 46% and 38%, respectively, were achieved.

The subcutaneous 9L tumor growth was also evaluated. The results of the subcutaneous 9L tumor growth delay experiments are presented below in Table III.

TABLE III

Subcutaneous 9L Tumor Growth Delay

| Treatment Group | Mean Days |
|---|---|
| Control Group* | — |
| UPHS | 1.5 ± 0.4 |
| BCNU | 5.8 ± 0.5 |
| BCNU/UPHS | 7.8 ± 0.6 |
| CTX | 9.1 ± 0.7 |
| CTX/UPHS | 14.0 ± 0.9 |
| CDDP | 9.4 ± 0.8 |
| CDDP/UPHS | 10.1 ± 0.8 |

TABLE III-continued

Subcutaneous 9L Tumor Growth Delay

| Treatment Group | Mean Days |
|---|---|
| IFOS | 10.4 ± 0.9 |
| IFOS/UPHS | 14.3 ± 1.0 |

*Mean days for the control group to reach 500 mm³ were 19.5 ± 0.5 days.

Administration of UPHS alone did not significantly alter growth of the subcutaneous tumors. Administration of UPHS prior to treatment with BCNU resulted in a 1.3-fold increase in tumor growth delay compared to treatment with BCNU along. Similarly, administration of UPHS solution prior to each injection of CTX resulted in a 1.5-fold increase in tumor growth delay compared to treatment with CTX alone. There was no substantial effect on the tumor growth delay produced by a single dose of CDDP by administration of UPHS prior to the drug. Like CTX, the tumor growth delay resulting from treatment with IFOS was increased 1.4-fold by prior administration of UPHS.

The chemotherapeutic agents examined in this study were all relatively small molecules which should not be subject to blood brain barrier exclusion on the basis of molecular weight or charge. Two of the drugs CTX and IFOS, are pro-drugs which undergo metabolism in the liver to form short-lived active alkylating species. It is interesting that CTX and IFOS which were very effective treatments for subcutaneously growing 9L tumors were the least effective treatments for intracranial 9L tumors. BCNU was least effective against subcutaneously growing 9L tumors but moderately effective against the intracranial 9L tumors. CDDP which was the most stable and aqueously soluble drug studied was very effective against both subcutaneous and intracranial 9L tumors.

The addition of UPHS to treatment with the antitumor alkylating agents improved the overall therapeutic outcome of treatment of the intracranial tumors to a greater degree than it did treatment of the subcutaneous tumors. One possible reason for this differential effect may be that the intracranial tumors are much smaller (by necessity) than the subcutaneous tumors at the time of treatment. Another possible reason for a greater improvement in the intracranial tumors by the combined treatment may be that the brain (and perhaps the brain tumor) is more highly vascularized than the subcutaneous tumor.

The greatest increases in therapeutic response upon addition of UPHS to treatment with the antitumor alkylating agents were seen with CTX and IFOS as evidenced by both increase in tumor growth delay and increase in life span. Both BCNU and CDDP treatments were improved to a greater degree, as determined by increase in life span, against the intracranial tumor than against the subcutaneous tumor.

EXAMPLE V

Lewis Lung Carcinoma

The Lewis lung tumor was carried in male C57BL mice (Taconic Laboratories, Germantown, N.Y.). For the experiments, $2 \times 10^6$ tumor cells prepared from a brei of several stock tumors were implanted subctaneously into the legs of male mice aged 8–10 weeks. By day 4 after tumor cell implantation, Lewis lung tumors began neovascularization. Animals bearing Lewis lung tumors were treated daily with intraperitoneal Mino (10 mg/kg), Diflun (15 mg/kg) or Sulin (15 mg/kg) on days 4–18 following tumor implantation. When the tumors had reached a volume of approximately 100 mm$^3$ (day 7 after tumor cell implantation), cytotoxic therapy was initiated.

Therapy consisted of treatment with an antitumor alkylating agent, an antitumor antimetabolite, a non-steroidal anti-inflammatory drug (NSAID) and/or UPHS. CDDP and PAM therapy consisted of a single 10 mg/kg CDDP or PAM dose administered by intraperitoneal injection on day 7. CTX therapy consisted of three successive 150 mg/kg CTX doses administered by intraperitoneal injections on days 7, 9 and 11. BCNU therapy consisted of three successive 15 mg/Kg BCNU doses administered by intraperitoneal injections on days 7, 9 and 11. Therapy with the antimetabolite 5-fluorouracil(5-FU) consisted of 4 successive 40 mg/kg 5-FU doses administered by intraperitoneal injections daily on days 7 to 11. The 5-FU was purchased from Sigma Chemical Co., St. Louis, Mo. Fourteen doses of 10 mg/kg of NSAID were administered daily by intraperitoneal injections on days 4 to 18. UPHS was injected into the tail vein in 8 ml/kg doses daily on days 7–11.

The progress of each tumor was measured thrice weekly until it had reached a volume of 500 mm$^3$. Tumor growth delay was calculated as the number of days required for each treated tumor to reach a volume of 500 mm$^3$ as compared with untreated control tumors. Each treatment group comprised six animals and the experiment was repeated three times.

On the twentieth day after the subcutaneous tumor implantation, the delay in Lewis Lung Carcinoma tumor growth was evaluated. The results are presented in Table IV. Tumor growth delay data is presented as the mean value ±SE calculated for the treatment group as compared with the control group.

Neither the UPHS nor the NSAIDS, without a cytotoxic agent, had any significant effect on the subcutaneous growth of Lewis lung carcinoma. The tumor growth delay produced by CTX treatment was substantially longer than that resulting from CDDP, PAM, BCNU or 5-FU. However, the growth delay effects from treatment with CTX or PAM were substantially increased, more than two-fold, by the addition of UPHS to the treatment. CDDP, BCNU and 5-FU treatment was also enhanced, to a lesser degree, by the addition of UPHS to treatment.

Addition of NSAIDs to the cytotoxic agents, delayed tumor growth in an amount slightly less than that produced by the addition of UPHS to the cytotoxic agents, with sulin providing the best NSAID results. Furthermore, the combination of cytotoxic agents, NSAIDs and UPHS typically yielded the best results for most combinations with the growth delay for each cytotoxic agent generally doubled.

TABLE IV

Lewis Lung Carcinoma Growth Delay

| Treatment Group | WITHOUT UPHS | | WITH UPHS | |
|---|---|---|---|---|
| | Mean Days | Lung Metastases (% Large) | Mean Days | Lung Metastases (% Large) |
| Control | — | 20(62) | 0.6 ± 0.3 | 18(72) |
| Mino | 0.8 ± 0.3 | 20(50) | 1.0 ± 0.4 | 20(65) |
| Diflun | 0.3 ± 0.2 | 20(51) | 0.9 ± 0.3 | 20(55) |
| Sulin | 1.2 ± 0.4 | 19(55) | 0.5 ± 0.3 | 21(57) |

TABLE IV-continued

Lewis Lung Carcinoma Growth Delay

| Treatment Group | WITHOUT UPHS | | WITH UPHS | |
|---|---|---|---|---|
| | Mean Days | Lung Metastases (% Large) | Mean Days | Lung Metastases (% Large) |
| CDDP | 4.5 ± 0.3 | 13(58) | 5.7 ± 0.4 | 13(40) |
| CDPP/Mino | 5.0 ± 0.3 | 11(48) | 7.3 ± 0.8 | 16(44) |
| CDDP/Diflun | 5.8 ± 0.5 | 15(37) | 7.7 ± 0.9 | 16(38) |
| CDDP/Sulin | 5.9 ± 0.5 | 13.5(44) | 8.9 ± 1.0 | 13(38) |
| CTX | 21.5 ± 1.7 | 12(40) | 43.1 ± 2.9 | 8(40) |
| CTX/Mino | 38.2 ± 2.9 | 6(33) | 44.9 ± 3.2 | 3(60) |
| CTX/Diflun | 31.5 ± 2.8 | 8(38) | 38.4 ± 2.9 | 7(50) |
| CTX/Sulin | 35.1 ± 2.6 | 10(30) | 39.6 ± 2.8 | 5(40) |
| PAM | 2.7 ± 0.3 | 13(48) | 6.8 ± 0.4 | 10(50) |
| PAM/Mino | 4.8 ± 0.4 | 11(50) | 12.8 ± 0.9 | 9.5(31) |
| PAM/Diflun | 5.0 ± 0.3 | 14(40) | 9.4 ± 0.8 | 8(50) |
| PAM/Sulin | 7.2 ± 0.4 | 12(48) | 12.9 ± 0.9 | 9(39) |
| BCNU | 3.6 ± 0.4 | 15.5(53) | 5.3 ± 0.5 | 9(61) |
| BCNU/Mino | 5.2 ± 0.6 | 15(38) | 7.1 ± 0.6 | 8.5(41) |
| BCNU/Diflun | 4.7 ± 0.5 | 12(50) | 9.3 ± 0.8 | 8(38) |
| BCNU/Sulin | 7.0 ± 0.6 | 12(30) | 11.6 ± 0.9 | 7(39) |
| 5-FU | 5.4 ± 0.4 | 21(52) | 6.3 ± 0.5 | 15(40) |
| 5-FU/Mino | 7.6 ± 0.6 | 18(30) | 10.7 ± 0.8 | 11(43) |
| 5-FU/Diflun | 6.5 ± 0.5 | 16.5(44) | 11.6 ± 0.9 | 9.5(53) |
| 5-FU/Sulin | 7.2 ± 0.6 | 15(36) | 13.2 ± 1.1 | 9(39) |

EXAMPLE VI

Effects of UPHS on Subcutaneous 9L Gliosarcoma Oxygenation

The procedures and materials of Example IV were employed, except as noted. In this Example, tumor $pO_2$ measurements were made under four conditions: 1) normal air breathing, 2) carbogen (95% $O_2$/5% $CO_2$) breathing, 3) 10 minutes post intravenous hemoglobin solution (8 ml/kg) administration with normal air breathing and 4) 15 minutes post the initiation of carbogen breathing after intravenous hemoglobin solution administration. Data collection through three tumor diameters accrued about 50 $pO_2$ measurements and took about 10 minutes. The $pO_2$ microelectrode was recalibrated in aqueous solutions saturated with air and 100% nitrogen after each data collection, therefore the $pO_2$ microelectrode was recalibrated 4 times during the course of the experiment. Recalibration requires about 15 minutes.

Therefore, the duration required for tumor $pO_2$ measurements under the four conditions tested was about one hour and 40 minutes.

Tissue oxygen measurements were made using a $pO_2$-Histograph (Eppendorf, Inc., Hamburg, Germany). The polarographic needle microelectrode was calibrated in aqueous solutions saturated with air and 100% nitrogen. The electrode was used for tumor measurements if there was less than 1% variation in current measurements upon repetition of the calibration cycle. For tumor measurements, the rat was anesthetized by an intraperitoneal injection of Ketaset (35 mg/kg) and xylazine (25 mg/kg) prepared in phosphate-buffered 0.9% saline. The animal was placed on a heating pad and covered with a blanket to maintain body temperature. Core temperature was measured with a rectal thermometer. The tumor site was shaved and tumor diameters measured with calipers. A small patch of skin about 4 cm from tumor was shaved and an incision was made allowing the reference electrode (Ag/AgCl-ECG) to be inserted subcutaneously and secured. The tumor was exposed by removing about 1 cm$^2$ of skin over the site. The tumor capsis was then perforated with a 20 gauge needle. The pO$_2$ microelectrode was positioned in the perforation.

The pO$_2$ microelectrode under computer control was placed 1 mm into the tissue and then retracted 0.3 mm. Probe current was then measured and after 1.4 seconds the probe moved forward again. The total length of the measurement path was determined by the size of the tumor. After the probe reached the end of its measurement path it automatically retracted. The probe was then repositioned in the same perforation at a different angle and stepwise measurements were again initiated. Three diameters were measured in each tumor for a total of 40-60.

The results of the oxygenation measurements are presented in Table V, below.

TABLE V

| Measurement Condition | Subcutaneous 9L Gliosarcoma Oxygenation | | | |
|---|---|---|---|---|
| | % of readings < 5 mmHg | 10th percentile | pO$_2$, mmHg Median | 90th percentile |
| W/out UPHS: | | | | |
| Air | 49 | 0.0 | 6.5 | 28 |
| Carbogen | 41 | 0.0 | 25 | 116 |
| With UPHS: | | | | |
| Air | 24 | 2.7 | 18 | 21 |
| Carbogen | 0 | 14.5 | 55 | 152 |

Oxygen tensions of less than 5 mmHg are considered severely hypoxic and probably represent regions of therapeutic resistance. Oxygen tensions in normally oxygenated tissues range from about 15-30 mmHg. Under normal air breathing conditions nearly half of the 9L tumor is severely hypoxic. Under carbogen breathing conditions the severely hypoxic regions were reduced to about 40% of the tumor while the median pO$_2$ increased about 4-fold to 25 mmHg. Administration of UPHS (8 ml/kg) markedly altered the oxygen profile of the tumors. With air breathing after administration of UPHS the percentage of severe hypoxia in the tumors was reduced to 24% and the median pO$_2$ reached 18 mm/Hg. The addition of carbogen breathing to administration of UPHS markedly increased the oxygenation of the tumor such that severe hypoxia was eliminated and oxygenation through 90% of the tumor was normal or greater than normal.

EXAMPLE VII

Comparison Between Effects of UPHS and a Perfluorocarbon Emulsion Employed in Combination with PAM The procedures and materials of Example I were employed except that Fluosol-DA was substituted for UPHS. Fluosol-DA was obtained from Alpha Therapeutics Corporation and is an emulsion consisting of 25% (w/v) of the following perfluorocarbons: 7 parts perfluorodecalin, 3 parts per perfluorotripropyliamine; Pluronic F-68 (2.7%, w/v); yolk phospholipids (0.4% w/v) as emulsifiers; and glycerol (0.8%, w/v) as a cryoprotective agent. The annex solution (electrolyte/bicarbonate solution) furnished the preparation with physiological osmolarity. The half-life of Fluosol-DA in vivo is about 12 hours.

The specific procedures employing Fluosol-DA have been described previously. See Teicher, B. A. et al., "Approaches to Defining the Mechanism of Fluosol-DA 20%/Carbogen Enhancement of Melphalan Antitumor Activity", Cancer Res. 47:513-518 (1987); Teicher, B. A. et al., "Differential Enhancement of Melphalan Cytotoxicity in Tumor and Normal t+Tissue by Fluosol-DA and Oxygen Breathing", Int. J. Cancer 36:585-589 (1985); and Teicher, B. A. et al., "Effects of Various Oxygenation Conditions on the Enhancement by Fluosol-DA of Melphalan Antitumor Activity", Cancer Res. 47:5036-5041 (1987).

When PAM (10 mg/kg) was administered to animals bearing the FSaIIC fibrosarcoma in combination with Fluosol-DA and air breathing a tumor growth delay of about 6.5 days was observed. If carbogen breathing for 1 hour post drug administration was added to therapy with Fluosol-DA and PAM a tumor growth delay of about 9.5 days resulted. Extending the carbogen breathing period to 6 hours did not alter the tumor growth delay produced by the PA< and Fluosol-DA combination (Teicher, B. A. et al., "Effect of Various Oxygenation Conditions and Fluosol-DA on Cancer Chemotherapeutic Agents", Biomat., Art. Cells and Art. Organs 6:533-546 (1988)), however, preparation of the PAM in the Fluosol-DA as a vehicle resulted in a much enhanced tumor growth delay of about 29.5 days with carbogen breathing. The addition of UPHS to treatment with PAM was not quite as effective as combining PAM with Fluosol-DA and carbogen breathing resulting in a tumor growth delay of about 6.9 days. The combination of UPHS and carbogen breathing with PAM was more effective than the combination of Fluosol-DA and carbogen breathing with PAM producing a tumor growth delay of about 11.1 days compared with about 9.5 days.

Six hours of carbogen breathing are necessary to obtain a significant enhancement in the growth delay of the FSaIIC fibrosarcoma produced by CTX. Teicher, B. A. et al., "The Effect of Fluosol-DA and Oxygenation Status on the Activity of Cyclophosphamide In Vivo" Cancer Chemother. Pharmacol. 21:286-291 (1988). In the case of this drug the growth delay of the FSaIIC tumor with the treatment combination of CTX (150 mg/kg) with Fluosol-DA and carbogen breathing for 6 hours was about 12 days compared with about 3.6 days with CTX alone. The 12 days of tumor growth delay obtained with this perfluorochemical emulsion/carbogen modulation of CTX was greater than the 7.4 days of tumor growth delay obtained with UPHS and air breathing with CTX but not as large as the 16.5 days of tumor growth delay obtained with the UPHS and carbogen breathing modulation of CTX.

Equivalents

Those skilled in the art will recognize or be able to ascertain, using no more than routine experimentation, many equivalents to the specific embodiments of the invention described herein. Such equivalents are intended to be covered by the following claims.

We claim:

1. A method for treating a tumor, which has oxygen heterogeneity, in a host with a chemotherapeutic agent which, when administered to said host, has an antitumor effect on said tumor, comprising:

a) administering to said host a hemoglobin solution in an amount sufficient to increase the antitumor effect of said chemotherapeutic agent;

b) administering to said host an enzyme cyclo-oxygenase inhibitor in an amount sufficient to inhibit cell regulation processes, thereby increasing the antitumor effect of said chemotherapeutic agent; and c) administering to said host an effective amount of said chemotherapeutic agent.

2. A method of claim 1 wherein said hemoglobin is bovine hemoglobin.

3. A method of claim 1 wherein said enzyme cyclo-oxygenase inhibitor is a non-steroidal anti-inflammatory drug.

4. A method of claim 3 wherein said non-steroidal anti-inflammatory agent is selected from the group consisting of minocycline, diflunisal and sulindac.

5. A method of claim 4 wherein said chemotherapeutic agent comprises an antitumor alkylating agent.

6. A method of claim 4 wherein said chemotherapeutic agent comprises an antitumor antimetabolite.

7. A method of claim 1 wherein said hemoglobin solution is nonemulsified.

8. A method of claim 1 wherein said hemoglobin solution has an endotoxin concentration of less than 0.5 endotoxin units per milliliter.

9. A method of claim 1 wherein said hemoglobin solution has a hemoglobin content of from about 5 to about 25 grams per deciliter; and.

10. A method of claim 1 wherein said hemoglobin solution has a methemoglobin content of less than 20 percent.

11. A method of claim 1 wherein said host is breathing air after administration of the chemotherapeutic agent.

12. A method for treating a tumor, which has oxygen heterogeneity, in a host with a chemotherapeutic agent which, when administered to said host, has an antitumor effect on said tumor, comprising:

a) administering to said host a nonemulsified ultrapurified polymerized hemoglobin solution in an amount sufficient to increase the antitumor effect of said chemotherapeutic agent;

b) administering to said host a non-steroidal anti-inflammatory drug in an amount sufficient to inhibit cell regulation processes, thereby increasing the antitumor effect of said chemotherapeutic agent; and c) administering to said host an effective amount of said chemotherapeutic agent.

13. A method of claim 12 wherein said nonemulsified ultrapurified polymerized hemoglobin solution is characterized by:

a) has an endotoxin concentration of less than 0.5 endotoxin units per milliliter;

b) a phospholipid concentration of less than about 1 nanogram per milliliter;

c) a hemoglobin molecular weight distribution of greater than about 90% in the range of 68,000–500,000 Daltons;

d) a hemoglobin content of from about 5 to about 25 grams per deciliter; and e) a methemoglobin content of less than 20 percent.

14. A method of claim 12 wherein said non-steroidal anti-inflammatory agent is selected from the group consisting of minocycline, diflunisal and sulindac.

15. A method for treating a tumor, which has oxygen heterogeneity, in a host with a chemotherapeutic agent which, when administered to said host, has an antitumor effect on said tumor, comprising:

a) administering to said host a hemoglobin solution in an amount sufficient to increase the antitumor effect of said chemotherapeutic agent;

b) administering to said host an enzyme cyclo-oxygenase inhibitor in an amount sufficient to inhibit cell regulation processes, thereby increasing the antitumor effect of said chemotherapeutic agent; and c) administering to said host an effective amount of said chemotherapeutic agent, wherein said host is breathing air after administration of the chemotherapeutic agent.

16. A method of claim 15 wherein said enzyme cyclo-oxygenase inhibitor is a non-steroidal anti-inflammatory drug.

17. A method of claim 15 wherein said hemoglobin solution has an endotoxin concentration of less than 0.5 endotoxin units per milliliter.

18. A method of claim 15 wherein said hemoglobin solution has a hemoglobin content of from about 5 to about 25 grams per deciliter.

19. A method of claim 15 wherein said hemoglobin solution has a methemoglobin content of less than 20 percent.

20. A method of claim 15 wherein said enzyme cyclo-oxygenase inhibitor comprises a non-steroidal anti-inflammatory agent selected from the group consisting of minocycline, diflunisal and sulindac.

* * * * *